United States Patent
Luboshitz et al.

[19]

[11] Patent Number: 5,954,721
[45] Date of Patent: Sep. 21, 1999

[54] DEVICES FOR PASSIVE MOTION OF JOINTS UNDER TRACTION

[75] Inventors: Shmuel Luboshitz, Raanana; Avraham Shekalim, Nesher; Itay Sela, Kiryat Tivon, all of Israel

[73] Assignee: Rimlon Ltd., Nazareth Elite, Israel

[21] Appl. No.: 08/948,362

[22] Filed: Oct. 10, 1997

[51] Int. Cl.$^6$ .................................................. A61B 17/56
[52] U.S. Cl. ............................................. 606/57; 606/58
[58] Field of Search ................................... 606/54, 55, 57, 606/58, 59, 70, 71; 602/16, 21

[56] References Cited

U.S. PATENT DOCUMENTS

| | | | |
|---|---|---|---|
| 5,100,403 | 3/1992 | Hotchkiss et al. | 606/56 |
| 5,391,167 | 2/1995 | Pong et al. | |

FOREIGN PATENT DOCUMENTS

| | | | |
|---|---|---|---|
| 1509072 | 9/1989 | U.S.S.R. | |
| 1795887 | 2/1993 | U.S.S.R. | |
| 2154143 | 9/1985 | United Kingdom | |
| 2229096 | 9/1990 | United Kingdom | 606/57 |

OTHER PUBLICATIONS

Krakauer et al, "Hinged Device for Fractures Involving The Proximal Interphalangeal Joint", *Clinical Orthopaedics and Related Research*,327: 29–37, 1996.

Schenck, R., "The Dynamic Traction Method", *Hand Clinics*, 10(2): 187–198, 1994.

Kearney et al, "The Therapist's Management of Intra–Articular Fractures", *Hand Clinics*, 10(2): 199–209, 1994.

Fahmy, N.R.M.., "Stockport Serpentine Spring System for the Treatment of Displaced Comminuted Intra–Articular Phalangeal Fractures", *J. Hand Surgery*, 15B(3): 303–311, 1990.

Fahmy et al, "The "S" Quatro in the Management of Fractures of the Hand", *J. Hand Surgery*, 17B: 321–331, 1992.

Fahmy et al, "Chronic Fracture Dislocations of the Proximal Interphalangeal Joint", *J. Hand Surgery*, 19B(6): 783–787, 1994.

Brochure, "S Quatro", Surgicraft Ltd., Redditch, Worcestershire B97 6HF, England.

Brochure, "Compass® Proximal Interphalangeal (PIP) JointHinge", Smith & Nephew Richards Inc., 1450 Brooks Rd., Memphis, TN 38116.

Advertisement for Pennig Dynamic Wrist Fixator, EBI Medical Sysytems 6 Upper Pond Rd., Patsappany, NJ.

Advertisement for Toronto Medical Corp., 901 Dillingham Rd., Pickering, Ont., Can., L1W 2Y5.

Advertisement for Danninger Medical Technology, Inc., 4140 Fisher Rd., Columbus, Ohio 43228–1067.

*Primary Examiner*—Michael Buiz
*Assistant Examiner*—Julian W. Woo
*Attorney, Agent, or Firm*—Mark M. Friedman

[57] ABSTRACT

A device for generating passive motion of a joint while applying traction has a proximal bracket for engaging a pin drilled into a proximal bone adjacent to the joint, and a distal bracket for engaging a pin drilled into a distal bone adjacent to the joint. The two brackets are connected by a tension-hinge mechanism which includes a hinge for permitting relative rotational movement of the brackets, and an adjustment mechanism. The adjustment mechanism is configured to allow substantially continuous adjustment of the distance between the hinge and at least one of the brackets so as to apply tension across the joint. The adjustment mechanism also includes a number of elastic elements deployed so as to allow elastic variation of the distance between the two brackets.

7 Claims, 17 Drawing Sheets

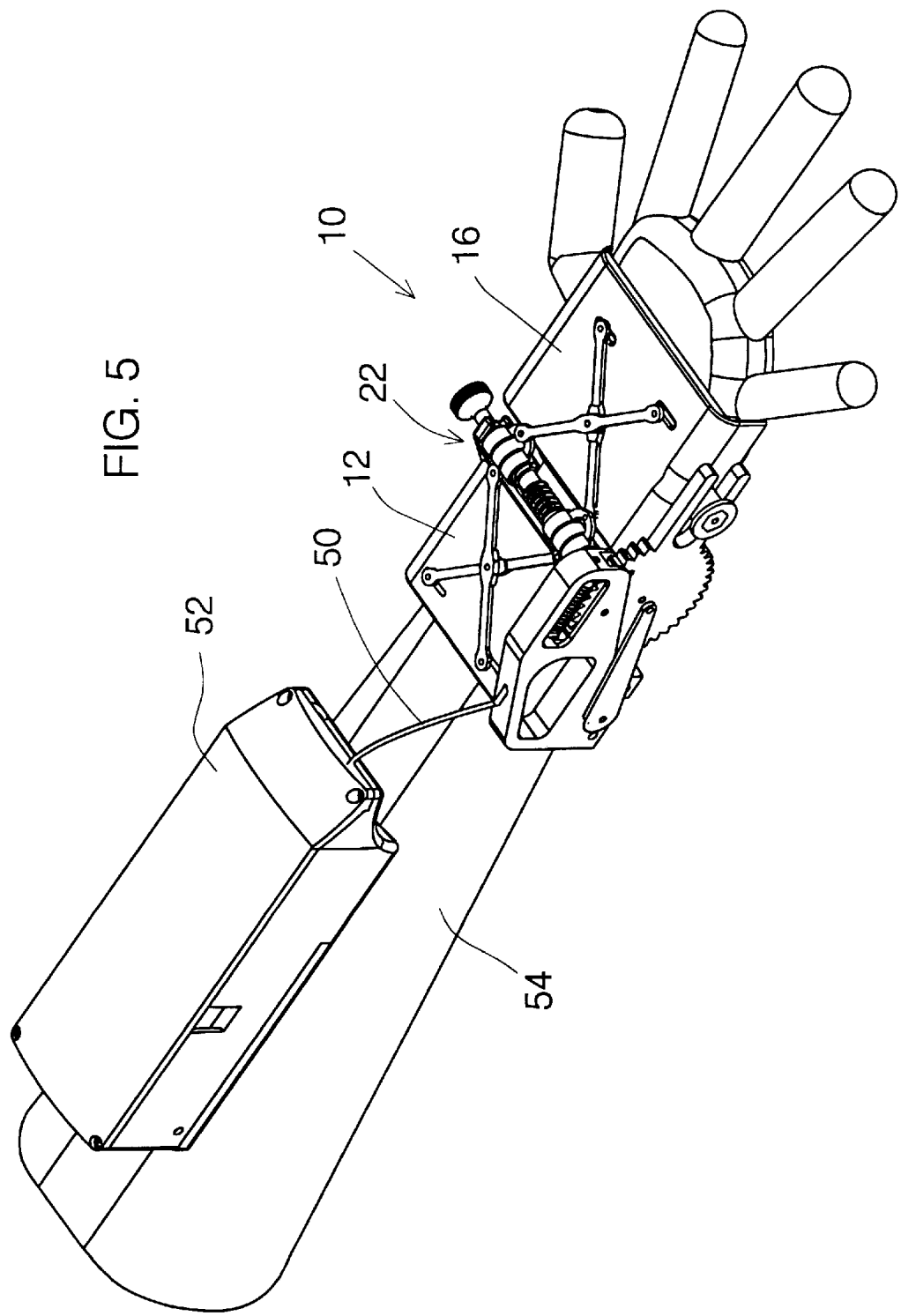

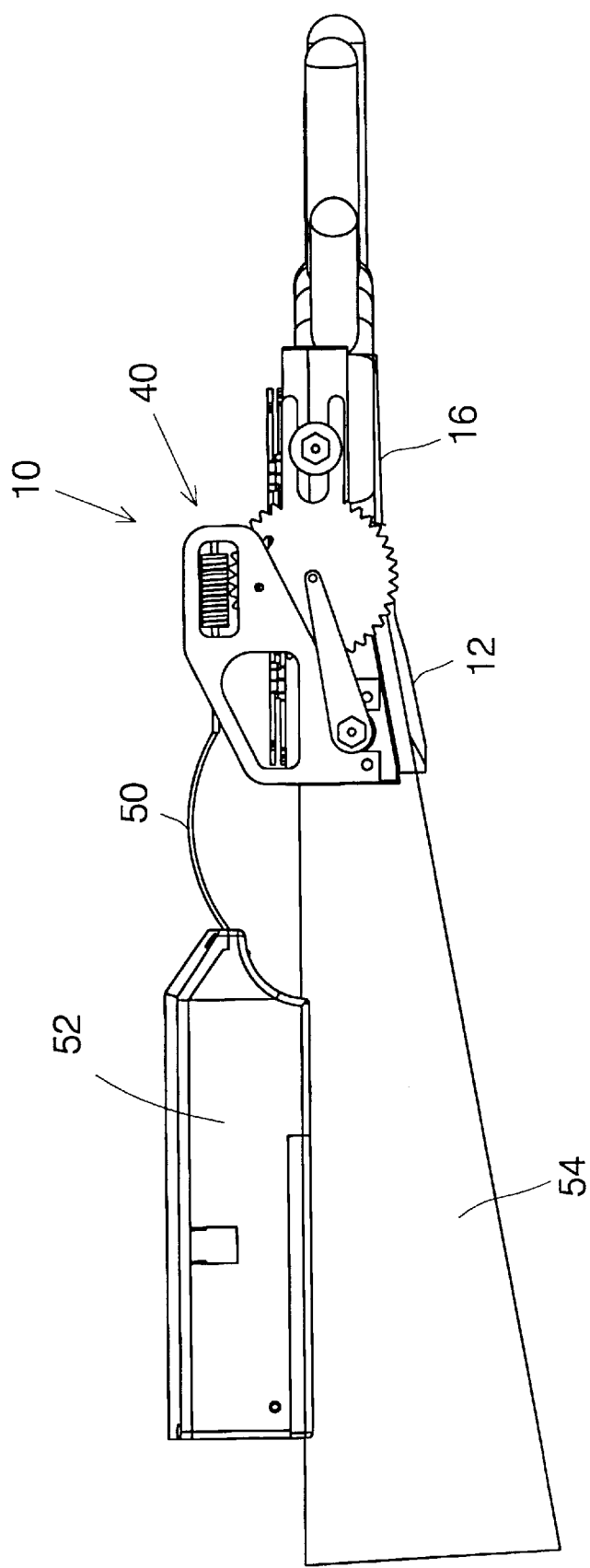

DEVICES FOR PASSIVE MOTION OF JOINTS UNDER TRACTION

FIELD AND BACKGROUND OF THE INVENTION

The present invention relates to orthopedic surgical devices and, in particular, it concerns devices for moving joints while maintaining traction across the joint.

It is known to employ traction across a joint in the treatment of intra-articular fractures. Especially where the bones are fragmented to an extent which precludes direct surgical procedures to stabilize the fragments, traction is known to induce ligamentotaxis in which the fragments re-align due to forces on their ligamentous and volar plate attachments.

Traction across a fractured joint can be applied by pushing apart pins implanted in each of the adjacent bones. An example of a simple system for applying traction in this manner is the "S Quattro Flexible Mini External Fixator" commercially available from Surgicraft Ltd., England.

It has been found, however, that prolonged application of traction across a fractured joint without movement of the joint frequently results in loss of joint mobility due to irregular re-molding of the joint surfaces. A number of attempts have therefore been made to develop traction systems which permit freedom of movement of the joint, referred to as "dynamic traction" systems.

One approach to dynamic traction is set out in an article entitled "The Dynamic Traction Method: Combining Movement and Traction for Intra-Articular Fractures of the Phalanges" by Robert R. Schenck, MD (*Hand Clinics* 10 (2) May 1994). This describes a system in which rubber bands are mounted between a transosseous wire located in the distal head of the middle phalanx and an external frame. In the primary example, the frame is formed as a large loop in the plane of movement of the joint. The point of connection of the rubber bands can then be slid manually around the loop to flex the joint while maintaining the applied traction. Also discussed are adaptations of existing continuous passive motion devices to apply tension, also by use of rubber bands.

A particular shortcoming of the dynamic traction systems discussed by Schenck is the imprecision and inconvenience of adjustment of the tension applied. Adjustment is achieved primarily by adding or removing rubber bands, thereby giving large discrete jumps in the amount of tension. Although a possibility of twisting the rubber bands is mentioned, no mechanism is provided for such an adjustment. The systems also require professional supervision, making them unsuitable for home-treatment.

A second approach to dynamic traction in systems is represented by a proximal interphalangeal joint hinge commercially available under the tradename Compass® from Smith & Nephew Richards Inc., USA. This hinge is secured by five pins drilled into the bones. Once positioned, an adjustment screw allows distraction of the joint. Once the desired degree of distraction is achieved, the pin blocks are fixed in position relative to the hinge. During normal operation of the hinge, no flexibility or elasticity is exhibited.

Although the Compass® system provides effectively continuously variable adjustment of the degree of distraction of the joint, the lack of flexibility in the system causes other shortcomings. Firstly, the hinge is extremely sensitive to misalignment. For this reason, a superfluous axial pin is drilled into the bone for alignment of the hinge. However, even with the extra pin, sufficiently precise positioning of the hinge is difficult to achieve. Additionally, even within the operative range of accuracy, a slight misalignment of the hinge may result in a large variation in the distraction of the joint during movement. The lack of flexibility also potentially makes the system breakable. Finally, passive movement of the joint is achieved by labor intensive manual operation of a worm-gear mechanism.

It is also interesting to note that none of the available systems is suitable for use with injuries to the wrist joint.

There is therefore a need for a dynamic traction device for treatment of intra-articular fractures which provides substantially continuous adjustability of traction applied elastically across the joint. It would also be advantageous to provide such a device in which passive motion is automated, and which is suited for use for wrist joints.

SUMMARY OF THE INVENTION

The present invention is a dynamic traction device for treatment of intra-articular fractures which provides substantially continuous adjustability of traction applied elastically across the joint. Preferred embodiments of the invention allow fully programmable control of a wide range of parameters relating both to the amount of traction applied and the range, speed and frequency of passive movement of the joint.

According to the teachings of the present invention there is provided, a device for generating passive motion of a joint while applying traction, the joint having been prepared by insertion of pins into a proximal and a distal bone adjacent to the joint, the device comprising: (a) a proximal bracket for engaging the pin of the proximal bone; (b) a distal bracket for engaging the pin of the distal bone; and (c) a tension-hinge mechanism connecting between the proximal bracket and the distal bracket, the tension-hinge mechanism including: (i) a hinge for permitting rotational movement of the distal bracket relative to the proximal bracket, and (ii) an adjustment mechanism for allowing substantially continuous adjustment of the distance between the hinge and at least one of the proximal bracket and the distal bracket so as to apply tension across the joint, the adjustment mechanism including an elastic element deployed so as to allow elastic variation of the distance between the proximal bracket and the distal bracket.

According to a further feature of the present invention, the adjustment mechanism includes a counter-threaded bolt, the counter-threaded bolt serving as a central pin for the hinge.

According to a further feature of the present invention, the counter-threaded bolt forms part of a scissors mechanism.

According to a further feature of the present invention, there is also provided an actuator mechanism deployed between the proximal bracket and the distal bracket for generating relative rotation between the proximal bracket and the distal bracket about the hinge.

According to a further feature of the present invention, the actuator mechanism includes a gear member attached to one of the proximal bracket and the distal bracket and a worm gear mounted with an axis of rotation fixed relative to the other of the proximal bracket and the distal bracket, the worm gear being engaged with the gear member.

According to a further feature of the present invention, the adjustment mechanism includes a gauge for indicating an extent of opening of the adjustment mechanism.

According to a further feature of the present invention, the joint is a wrist joint, the proximal bracket including upper and lower abutment surfaces for abutting upper and lower surfaces of a forearm of a patient and the distal bracket includes upper and lower abutment surfaces for abutting upper and lower surfaces of a hand of the patient.

BRIEF DESCRIPTION OF THE DRAWINGS

The invention is herein described, by way of example only, with reference to the accompanying drawings, wherein:

FIG. 5 is a schematic isometric view of the device of FIG. 1 in use;

FIG. 6 is a schematic side view of the device of FIG. 1 in use;

DESCRIPTION OF THE PREFERRED EMBODIMENTS

Figure 1:
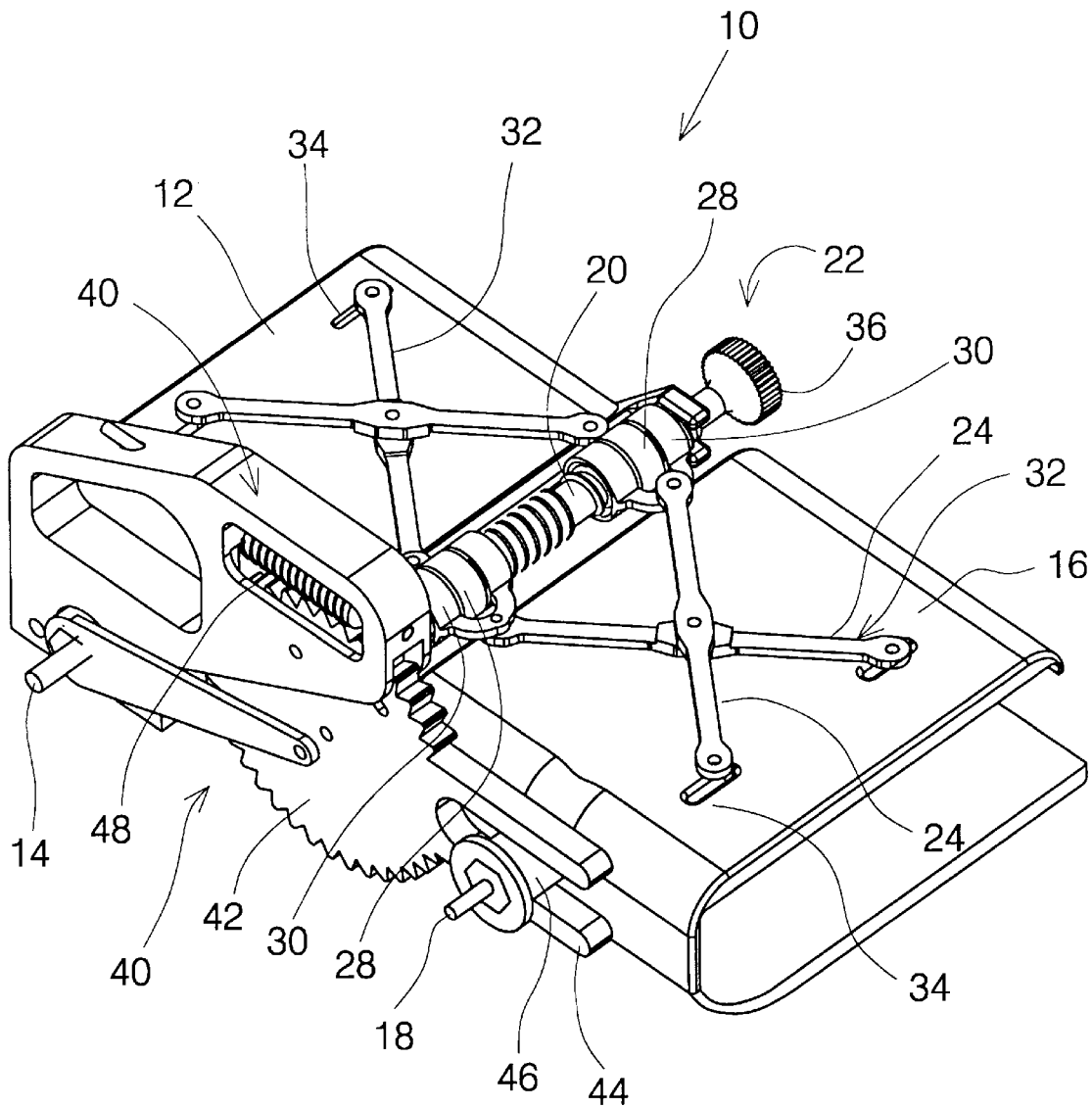
FIG. 1 is an isometric view of a first embodiment of a dynamic traction device, constructed and operative according to the teachings of the present invention, for use in surgical treatment of intra-articular fractures in a wrist joint.
Figure 2:
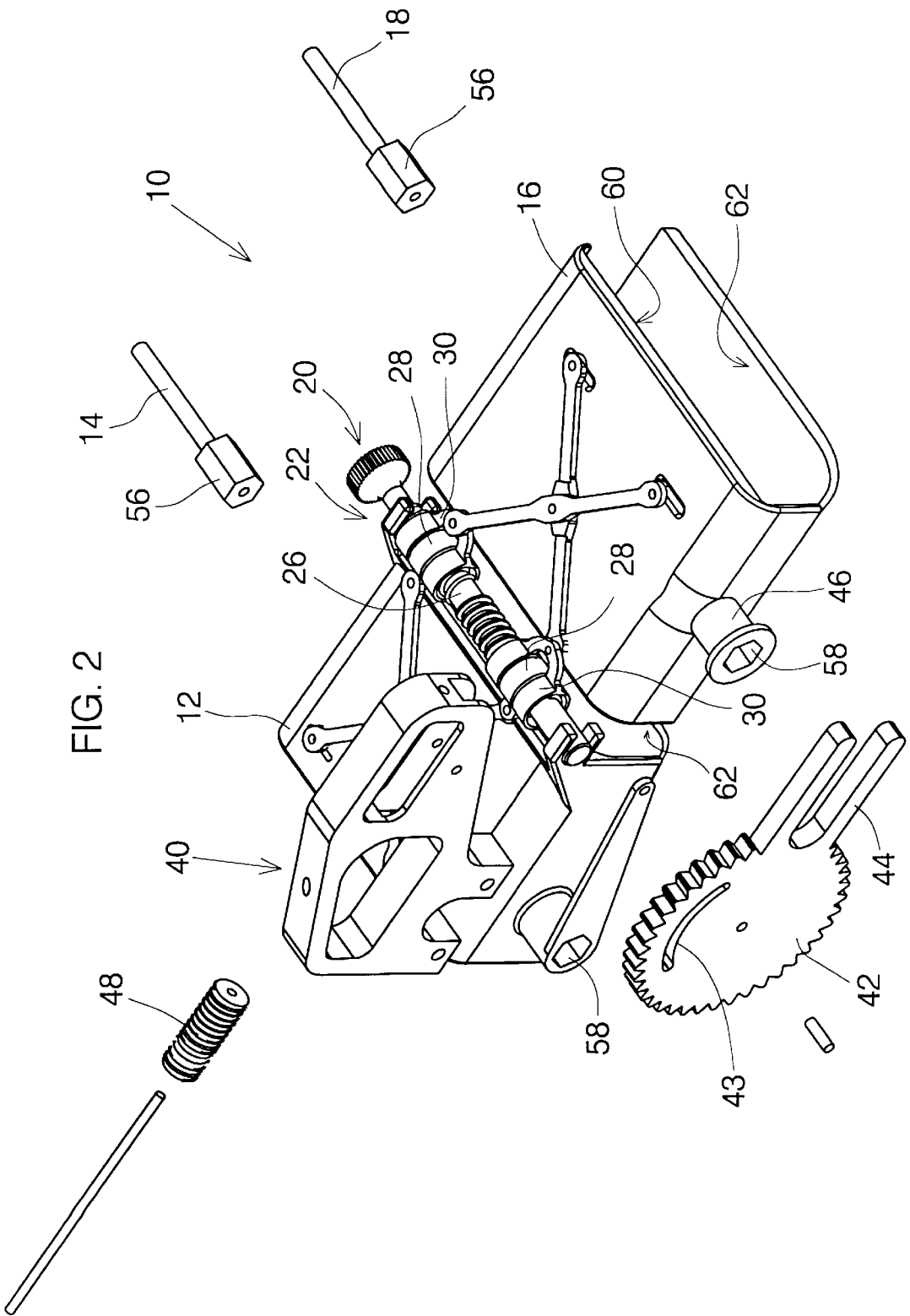
FIG. 2 is a partially exploded isometric view of the device of FIG. 1.
Figure 4:
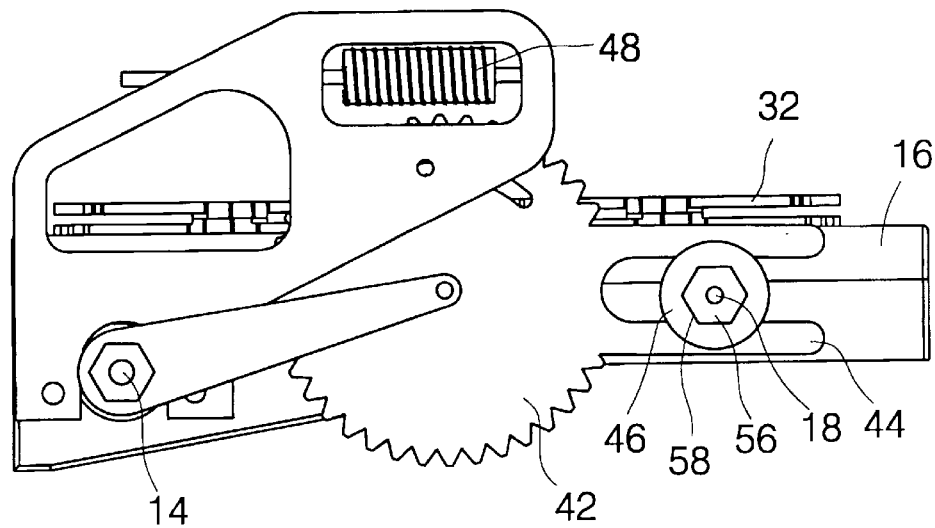
FIG. 4 is a side view of the device of FIG. 1.
Figure 3:
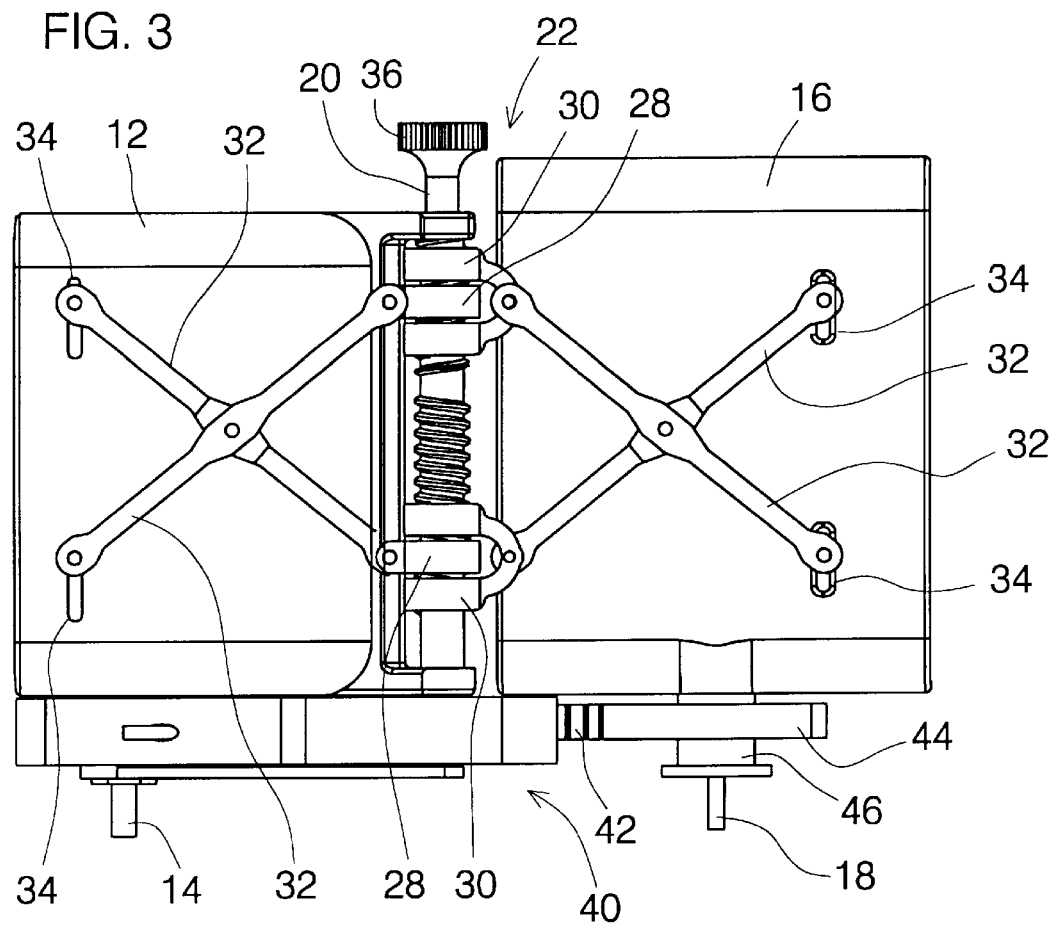
FIG. 3 is a plan view of the device of FIG. 1.
Figure 7:
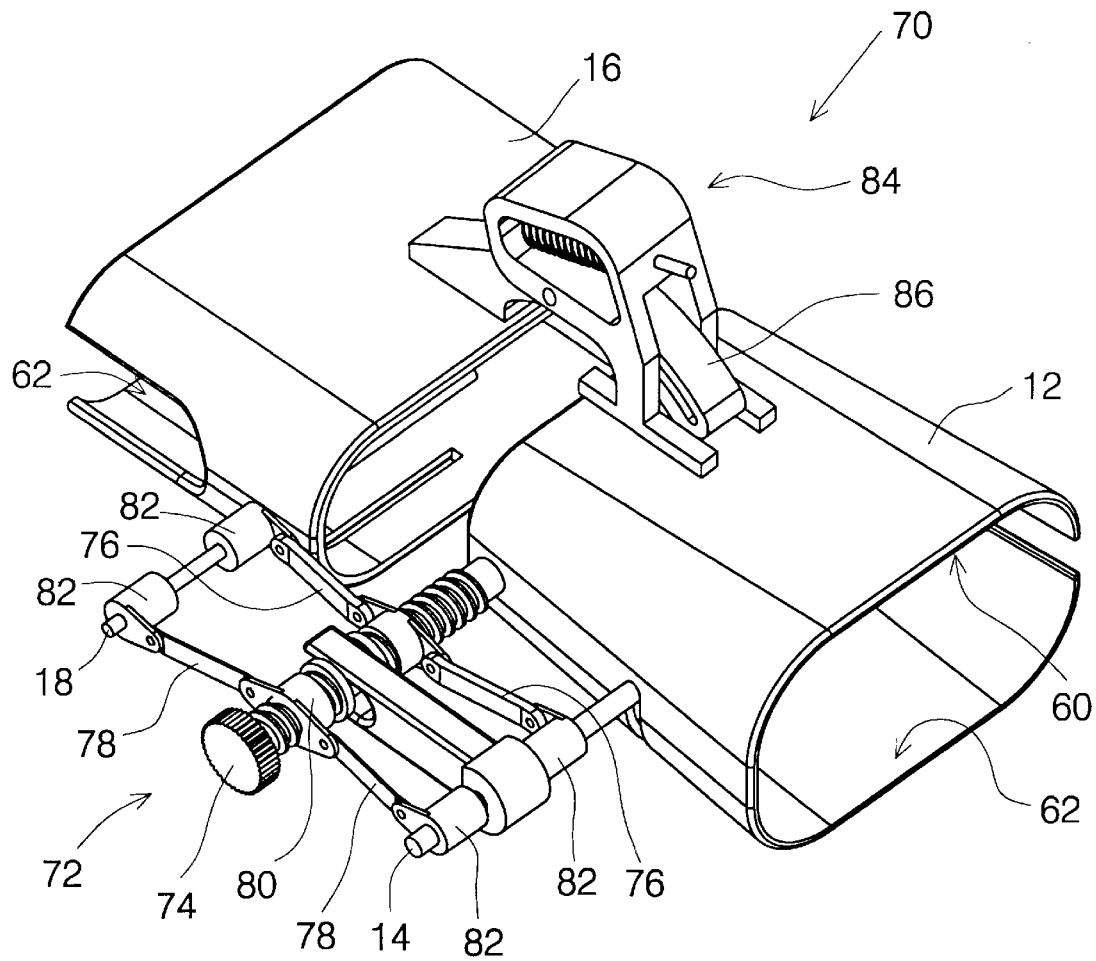
FIG. 7 is an isometric view of a second embodiment of a dynamic traction device, constructed and operative according to the teachings of the present invention, for use in surgical treatment of intra-articular fractures in a wrist joint.
Figure 9:
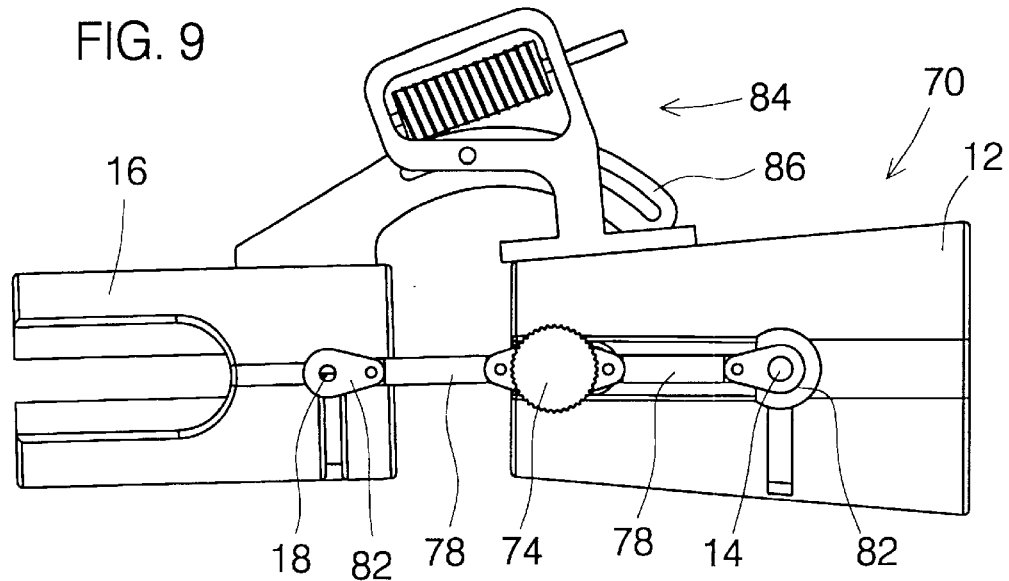
FIG. 9 is a side view of the device of FIG. 7.
Figure 8:
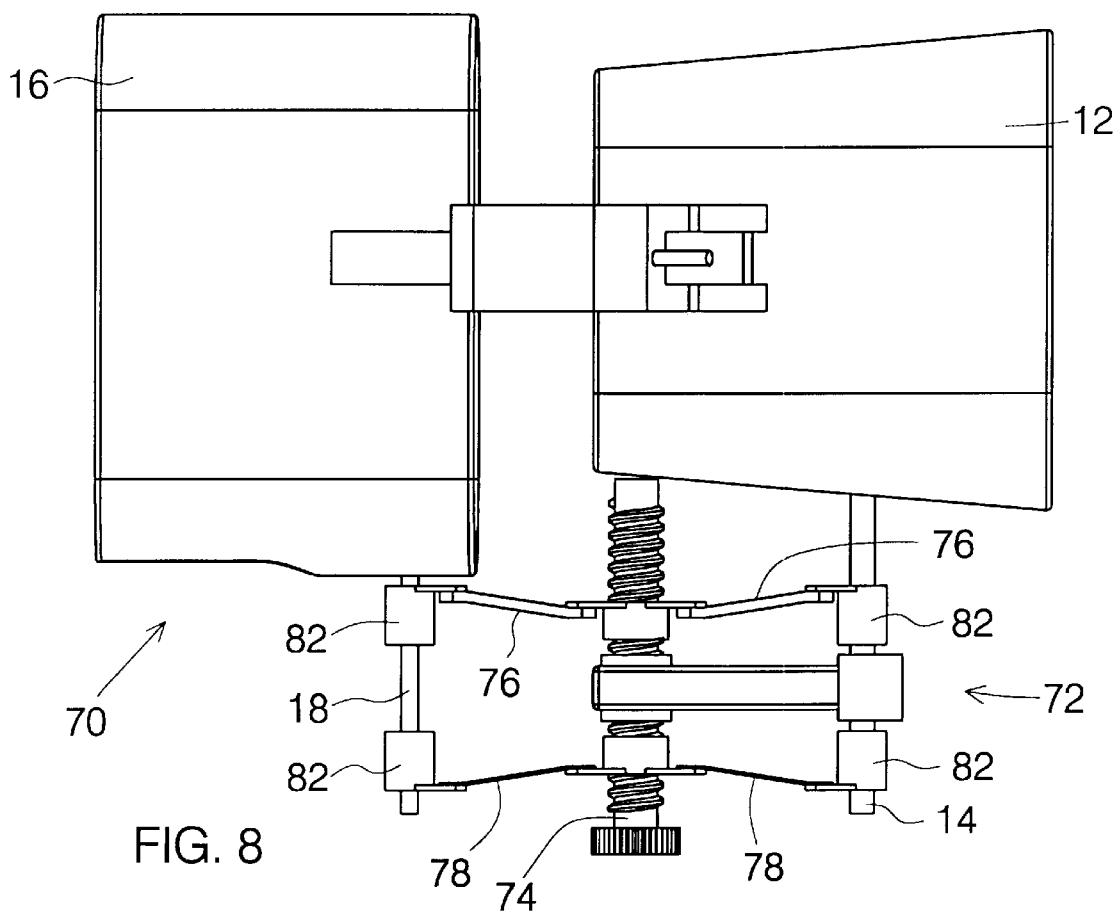
FIG. 8 is a plan view of the device of FIG. 7.
Figure 10:
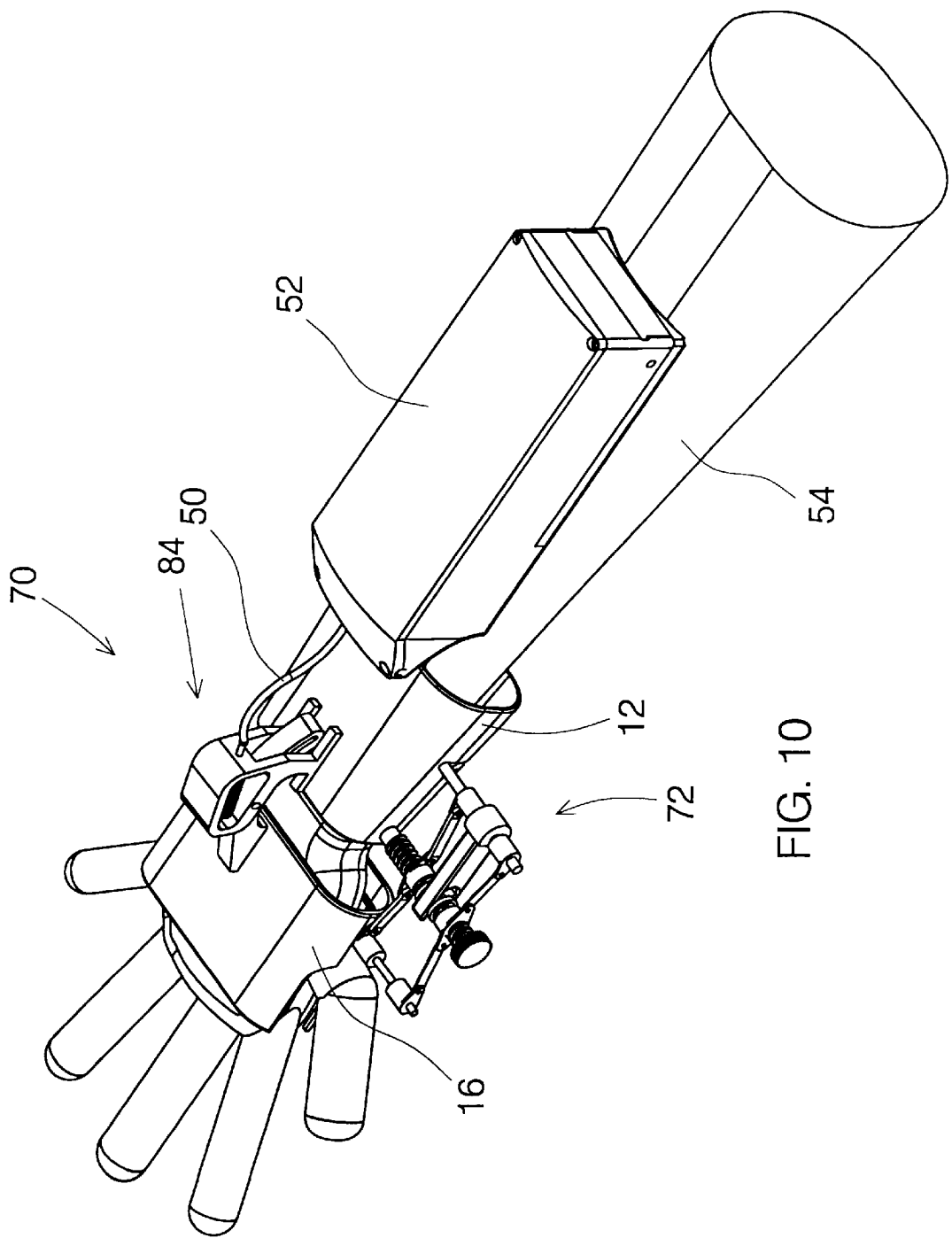
FIG. 10 is a schematic isometric view of the device of FIG. 7 in use.
Figure 11:
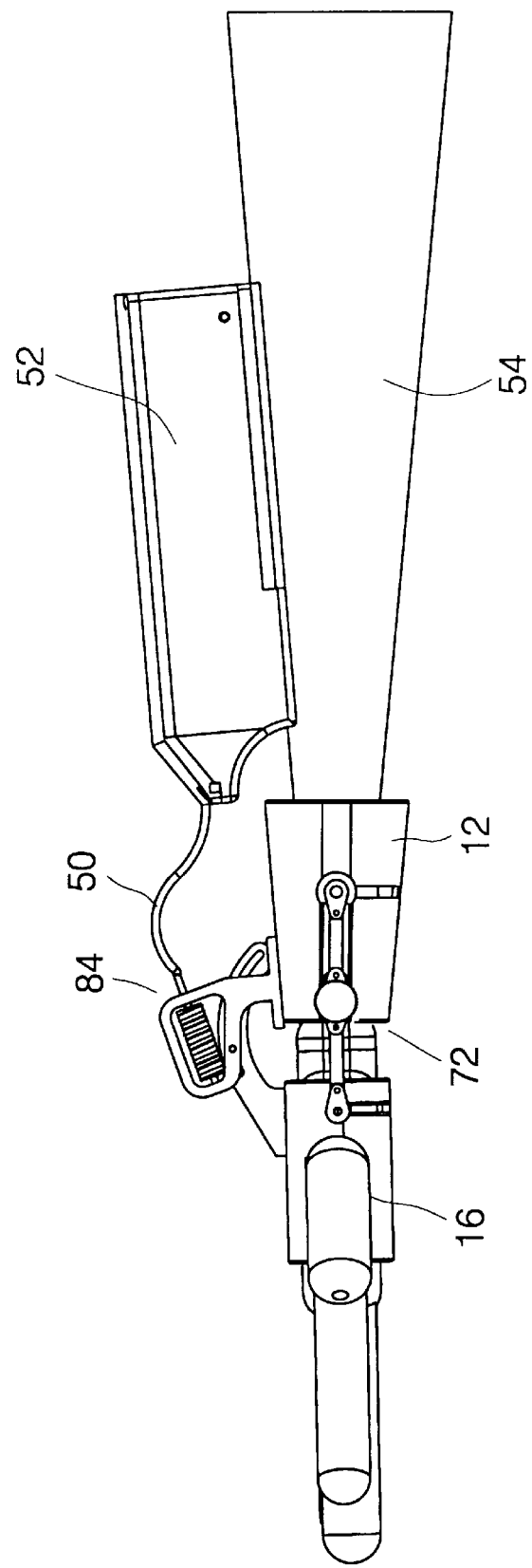
FIG. 11 is a schematic side view of the device of FIG. 7 in use.
Figure 12:
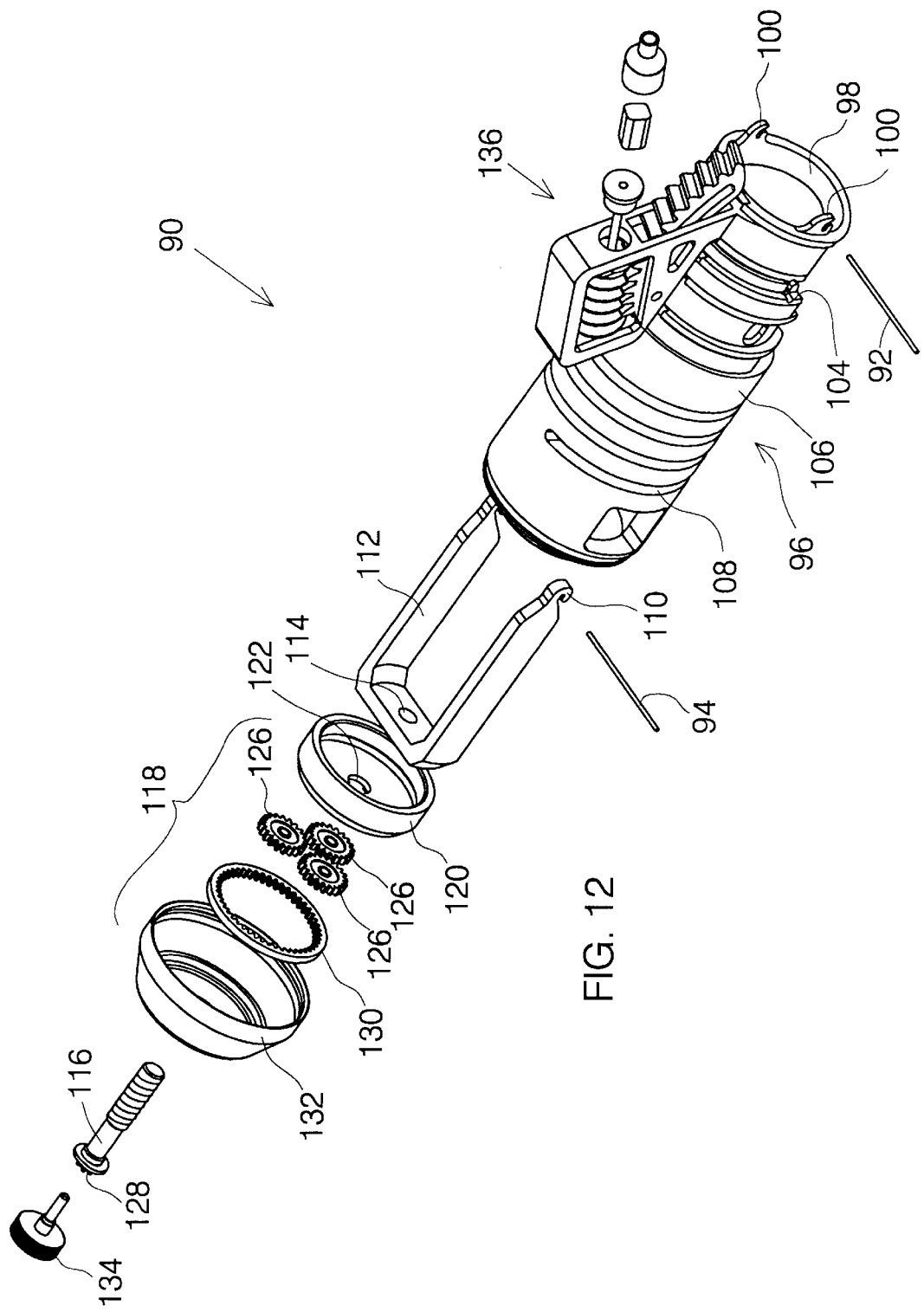
FIG. 12 is a first exploded isometric view of a third embodiment of a dynamic traction device, constructed and operative according to the teachings of the present invention, for use in surgical treatment of intra-articular fractures in an inter-phalangeal joint.
Figure 13:
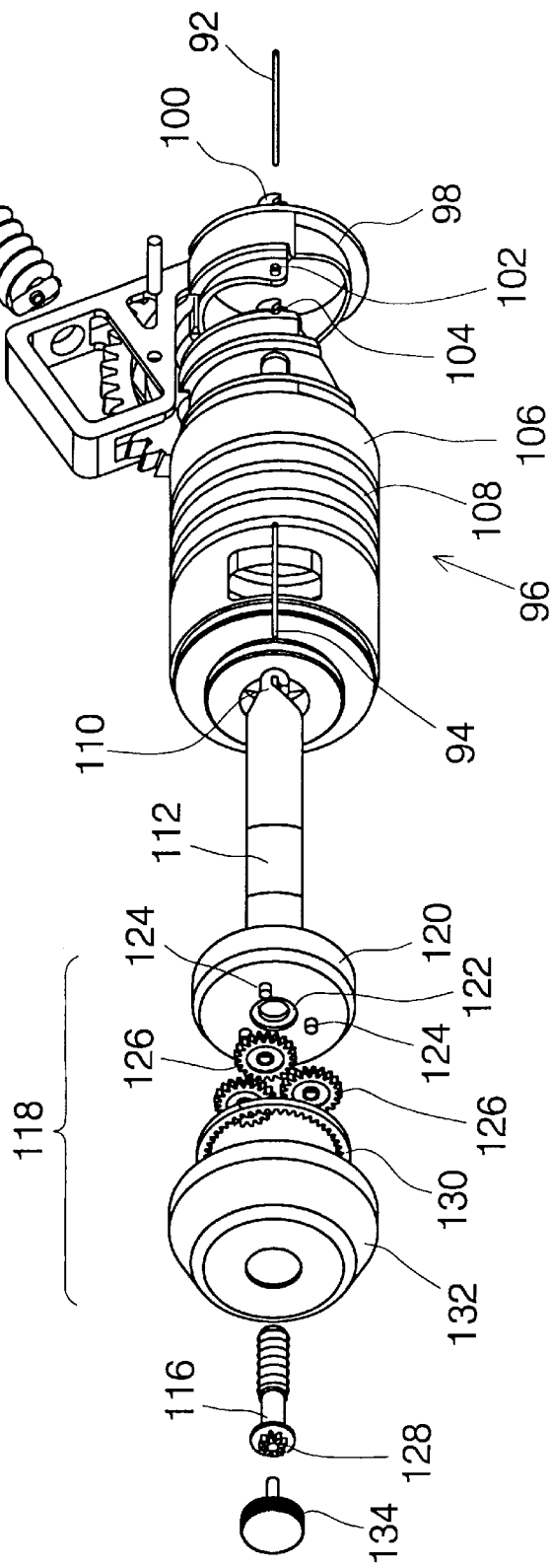
FIG. 13 is a second exploded isometric view of the device of FIG. 12.
Figure 15:
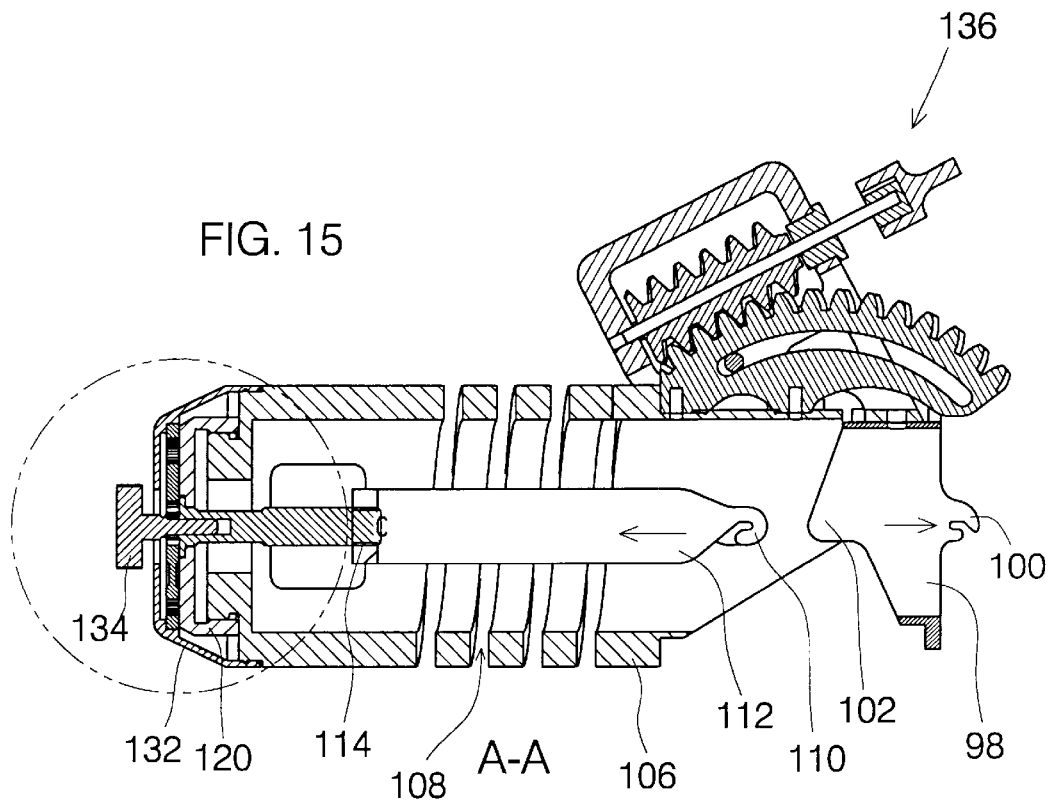
FIG. 15 is a side cross-sectional view of the device of FIG. 12.
Figure 14:
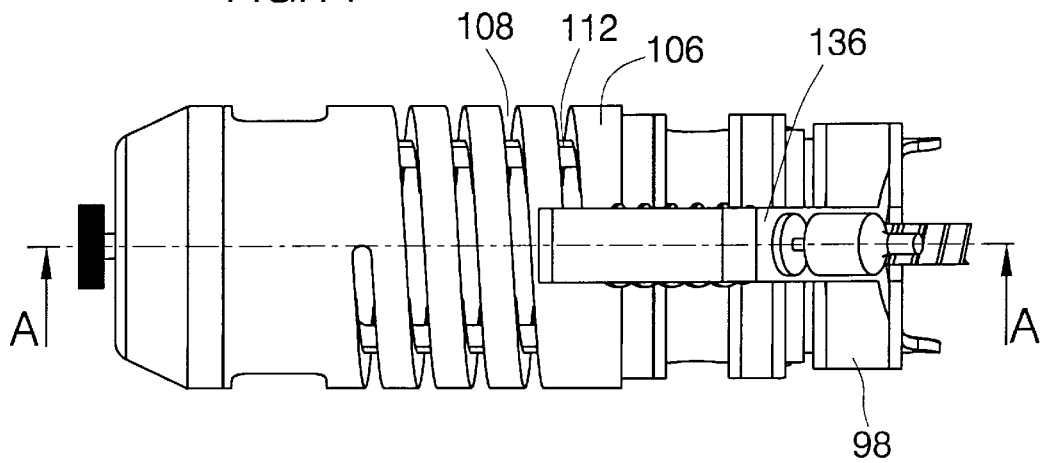
FIG. 14 is a plan view of the device of FIG. 12.
Figure 16:
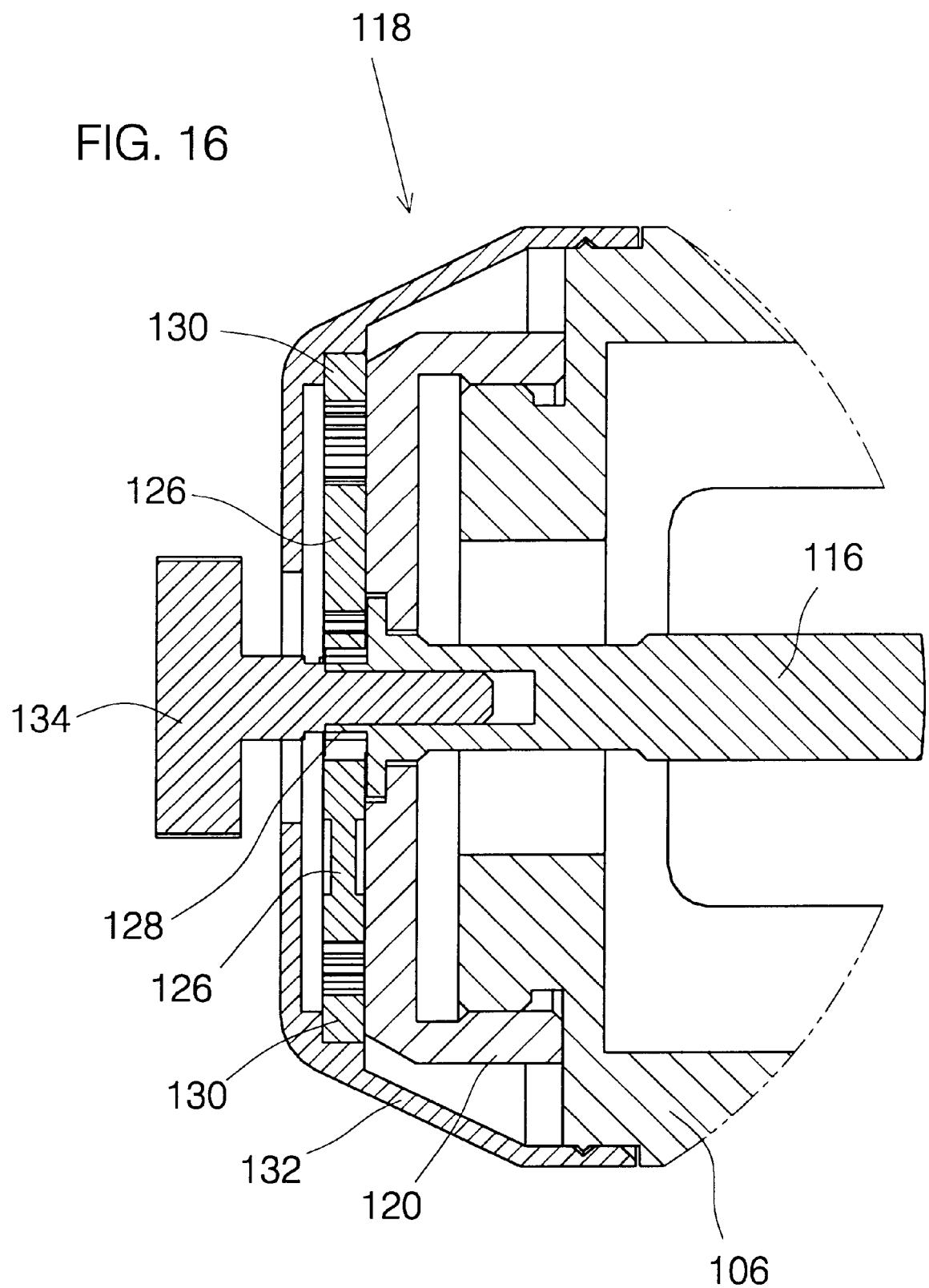
FIG. 16 is an enlarged view of a region of FIG. 15.

The present invention is a dynamic traction device for treatment of intra-articular fractures.

The principles and operation of devices according to the present invention may be better understood with reference to the drawings and the accompanying description.

Referring now to the drawings, FIGS. 1–6 show a first embodiment of a device, generally designated 10, constructed and operative according to the teachings of the present invention, for generating passive motion of a joint while applying traction.

Generally speaking, device 10 has a proximal bracket 12 for engaging a pin 14 drilled into a proximal bone adjacent to the joint, and a distal bracket 16 for engaging a pin 18 drilled into a distal bone adjacent to the joint. Brackets 12 and 16 are connected by a tension-hinge mechanism which includes a hinge 20 for permitting relative rotational movement of the brackets, and an adjustment mechanism 22. Adjustment mechanism 22 is configured to allow substantially continuous adjustment of the distance between hinge 20 and at least one of brackets 12 and 16 so as to apply tension across the joint. Adjustment mechanism 22 also includes a number of elastic elements 24 deployed so as to allow elastic variation of the distance between brackets 12 and 16.

It will be appreciated that the combination of continuous adjustability and elasticity provides considerable advantages over the prior art references described above. Specifically, the adjustment may be performed quickly and precisely to achieve the desired traction. At the same time, the elasticity renders the precise location of hinge 20 much less critical.

It is a preferred feature of most embodiments of the present invention that most or all of the device is produced from X-ray transparent materials to allow imaging of the injured joint while the device is in place. A range of suitable plastics and other polymer materials generally known in the art may be used.

Turning now to the features of device 10 in more detail, adjustment mechanism 22 includes a counter-threaded bolt 26 which serves as a central pin for hinge 20. "Counter-threaded" is used in this context to refer to a bolt which is threaded in a right-handed sense in one region and a left-handed sense in another region. Mounted on bolt 26 are two oppositely threaded locating collars 28, each engaged between the rings of a double ring washer bracket 30. Attached to locating collars 28 are a first pair of centrally pivoted scissor arms 32. A second pair are attached to brackets 30. The free ends of scissor arms 32 have downwardly projecting pins which engage transverse slots 34 in proximal and distal brackets 12 and 16. This structure functions as a double scissors mechanism so that rotation of an adjustment knob 36 formed at the end of bolt 26 simultaneously pushes brackets 12 and 16 towards or away from hinge 20.

As mentioned above, adjustment mechanism 22 includes a number of elastic elements 24 deployed so as to allow elastic variation of the distance between brackets 12 and 16. In this embodiment, elastic elements 24 are preferably implemented as the entirety of one or both pairs of scissor arms 32. In other words, the material and design of the scissor arms are chosen to provide the required degree of flexibility. Thus, as knob 36 is tightened, brackets 12 and 16 move apart until mechanical resistance is encountered. Further tightening of knob 36 beyond this point causes some elastic deformation of arms 32, thereby elastically applying tension (traction) between brackets 12 and 16. The amount of tension is controlled in a continuous manner by the angle through which knob 36 is turned.

Alternatively, localized flexible regions or spring elements may be incorporated within one or both pairs of arms 32 to provide the required elasticity.

Preferably, device 10 also features an actuator mechanism 40 deployed between proximal bracket 12 and distal bracket 16 for generating relative rotation between them about hinge 20. This allows application of passive motion therapy while maintaining traction across a joint.

Actuator mechanism 40 preferably includes a gear member 42, rotatably mounted near hinge 20. Gear member 42 has a fork-like extension 44 which engages a projection 46 from one of the brackets, in this case, distal bracket 16. Engaged with gear member 42 is a worm gear 48 the axis of which is mounted relative to the other bracket, in this case, proximal bracket 12. Rotation of worm gear 48 causes gear member 42, and hence distal bracket 16 to rotate relative to proximal bracket 12. Preferably, gear member 42 has an arcuate slot 43 (see FIG. 2) at constant radius from the center of the gear member which is engaged by a pin of the worm gear housing. This ensures that the movement of the actuator mechanism is limited to an arcuate path, preventing any linear displacement between brackets 12 and 16 which could otherwise be caused.

Preferably, worm gear 48 is driven through a flexible drive cable 50 by a portable control unit 52 which can be strapped to the arm 54 of a patient (see FIGS. 5 and 6). Control unit 52 typically includes an electric motor driven from batteries under the control of a programmable microprocessor unit. This allows a surgeon to set and modify parameters of a passive exercise treatment program, including the extent and speed of both downward and upward movements, the delay between successive movements, the length of each treatment session and the time between sessions. All of these parameters may be programmed to change progressively or in steps during the course of the treatment. When necessary, adjustment or reprogramming can be performed.

In an alternative implementation, worm gear 48 may be manually operated to achieve passive movement of the joint.

As mentioned above, device 10 is skeletally anchored by pins 14 and 18 which are inserted into a proximal and a distal bone adjacent to the damaged joint. In order to prevent angular distortion of the joint under traction, pins 14 and 18 are preferably mounted in elongated plugs 56 which are received within corresponding elongated sockets 58 of brackets 12 and 16.

Although device 10 can be used with minor adaptations for a wide range of different joints, the particular example shown here is designed for use with a wrist joint. In order to impart movement to the joint for passive motion therapy, brackets 12 and 16 provide upper and lower abutment surfaces 60 and 62 which apply pressure against the forearm and hand of the patient.

Turning now to FIGS. 7–11, as second embodiment of a device, generally designated 70, constructed and operative according to the teachings of the present invention, for generating passive motion of a joint while applying traction. Device 70 is similar in principle to device 10, but employs a different design of adjuster mechanism 72 mounted directly between pins 14 and 18.

Specifically, adjuster mechanism 72 also has a central bolt 74 which serves as a hinge. Between bolt 74 and each of pins 14 and 18, two spring rods 76 and 78 are mounted at an angle. The attachment of the spring rods to bolt 74 is through threaded collars 80, while the attachment to the pins is at sleeves 82 fixed by pressure fitting. Rotation of bolt 74 causes collars 80 to move along the bolt, thereby changing the angle of spring rods and hence urging pins 14 and 18 away from bolt 74.

Spring rods 76 which are closer to the proximal and distal brackets are preferably relatively stiff, whereas rods 78, closer to the outer ends of the pins, are preferably relatively flexible. As a result, when adjustment mechanism 72 is tightened, the outward force caused by rods 76 is greater than that caused by rods 78, tending to force the implanted ends of the pins apart. This counters the tendency of the adjustment system to generate angular distortion in the joint.

The thread of bolt 74 may be opposite for the two collars 80, causing them to push outwards simultaneously. Alternatively, co-directional threading can be used. This causes spring rods 78 to draw the ends of pins 14 and 18 inwards while stiffer spring rods 76 push outwards, thereby further enhancing the angular distortion compensation of adjustment mechanism 72.

Device 70 also features an actuator mechanism 84. Actuator mechanism 84 is similar to mechanism 40 described above, except that the gear element is here implemented as an arched rack 86. In all other respects, the features and operation of device 70 will be fully understood by analogy to that of device 10 described above.

Turning now to FIGS. 12–20, there will be described a third embodiment of a device, generally designated 90, constructed and operative according to the teachings of the present invention, for generating passive motion of a joint while applying traction. This embodiment employs similar principles to those of the embodiments described above, but in a design particularly suited for inter-phalangeal joints. An additional feature illustrated by this embodiment is the provision of a gauge for indicating the extent of opening of the adjustment mechanism.

As in the previous embodiments, device 90 is skeletally anchored by two pins 92 and 94, in this case, inserted transosseously. The two brackets and the tension-hinge mechanism are all formed as an articulated hollow housing 96 which is mounted around the finger. A proximal section 98 of housing 96 features sockets 100 within which proximal pin 92 engages. Projections 102 from proximal section 98 engage hinge sockets 104 of an elongated distal section 106 of housing 96, thereby forming a hinge. Distal section 106 is formed with cut-out walls to as to form a spring structure. In the case illustrated here, a spiral cut-out 108 is formed to give distal section 106 a helical spring structure. Parenthetically, it should be noted that the term "cut-out" is used here to describe the final structure independent of the method used to generate it. Thus, distal section 106 may be produced directly with the required cut-outs by a range of conventional production techniques including, but not limited to, injection molding. Alternatively, a subsequent "cutting" procedure may be employed.

The ends of distal pin 94 are secured by hooks 110 at the ends of a fork 112 which is designed to extend along the sides of a patient's finger. The central region of fork 112 features a threaded opening 114 which receives the threaded end of an adjustment bolt 116 which is seated in a cap assembly 118 at the end of distal section 106.

It will now be appreciated that device 90 provides continuously adjustable elastic traction across a joint while permitting freedom of motion. Specifically, tightening of adjustment bolt 116 draws fork 112, and hence pin 94, towards cap assembly 118. This movement applies compression to the spring structure of distal section 106. This compressive force is transferred through the hinge to proximal section 98 and proximal pin 92. The result is traction applied between pins 92 and 94 corresponding to the extent of elastic compression in distal section 106.

It is a preferred feature of this and other embodiments of the device of the present invention that a gauge is provided for indicating the extent of opening of the adjustment mechanism. A simple example of such a gauge, illustrated here as part of cap assembly 118, will now be described with reference particularly to FIGS. 12, 13 and 16.

Thus, cap assembly 118 has an inner cap 120 which clips firmly onto a projecting rim of distal section 106. Inner cap 120 has a central opening 122 with a recessed rim which forms a seat for the flange of adjustment bolt 116. Three projections 124 provide central mounting points for three gear wheels 126 which form a planetary gear arrangement with a toothed head 128 of adjustment bolt 116. Engaged around the outer periphery of gear wheels 126 is an internally toothed wheel 130 on which an outer cover 132 sits. A projecting adjustment knob 134 engages a non-circular hole in the head of adjustment bolt 116 to facilitate manual rotation of the bolt.

The step-down effect of the planetary gear arrangement is such that outer cover 132 turns a small fraction of a revolution for each full revolution of adjustment bolt 116. By providing a pointer and scale arrangement between outer cover 132 and the adjacent part of distal section 106, the extent of rotation of outer cover 132 serves as a gauge for indicating the extent of tightening of the device. Optionally, part or all of outer cover 132 can be designed to be easily turned by hand to allow calibration of the gauge. In this case, knob 134 is turned through its range of free movement to take up any slack until the first mechanical resistance is felt. The scale is then set to its zero mark. The subsequent tightening indicated by the gauge is then a true indication of the traction being applied across the joint.

Preferably, device 90 also features an actuator mechanism 136 and control unit 138, structurally analogous and functionally equivalent to actuator mechanism 84 and control unit 52 described above.

Figure 17:
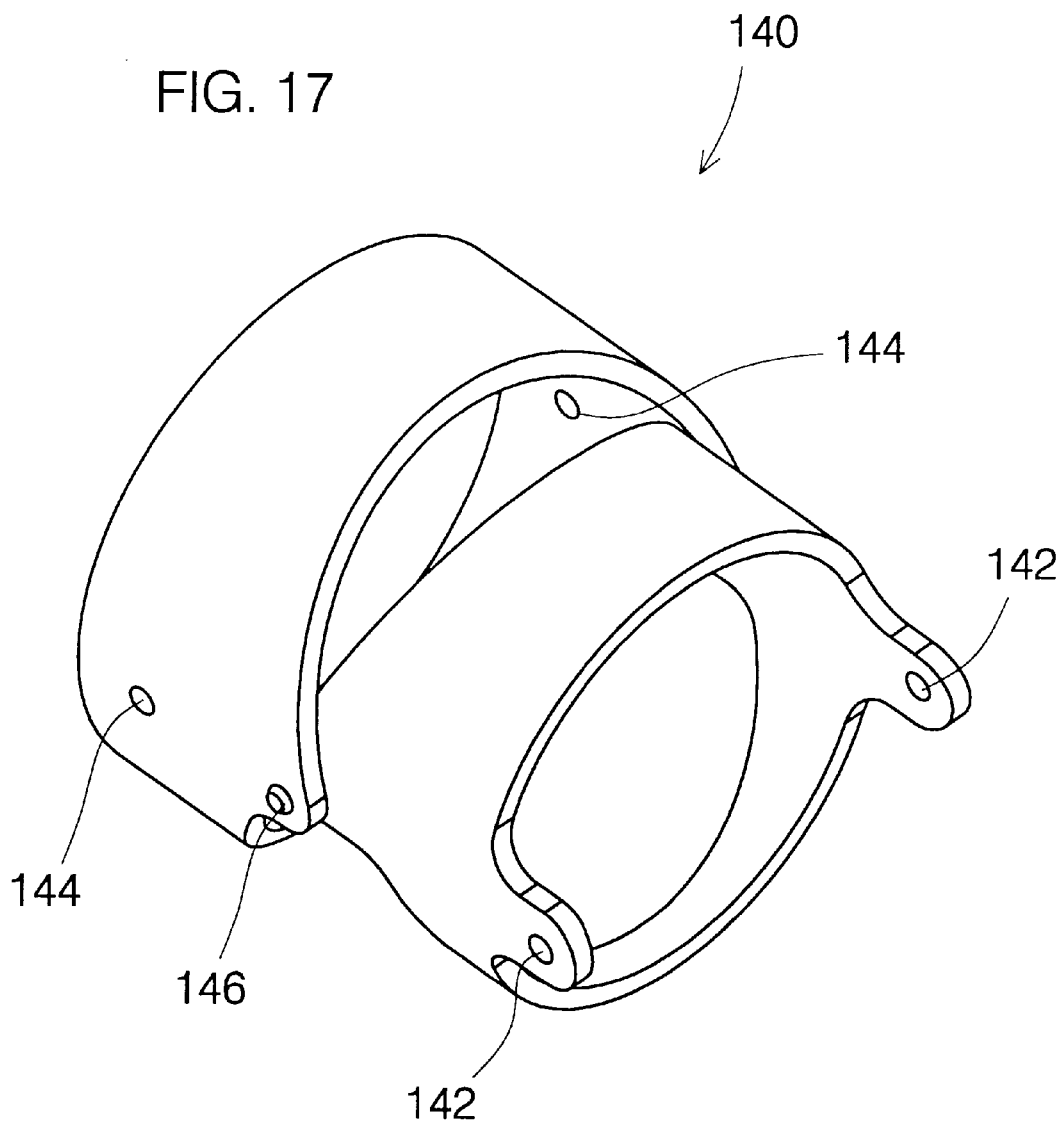
FIG. 17 is an isometric view of a template for use in locating pins for use with the device of FIG. 12.
Figure 18:
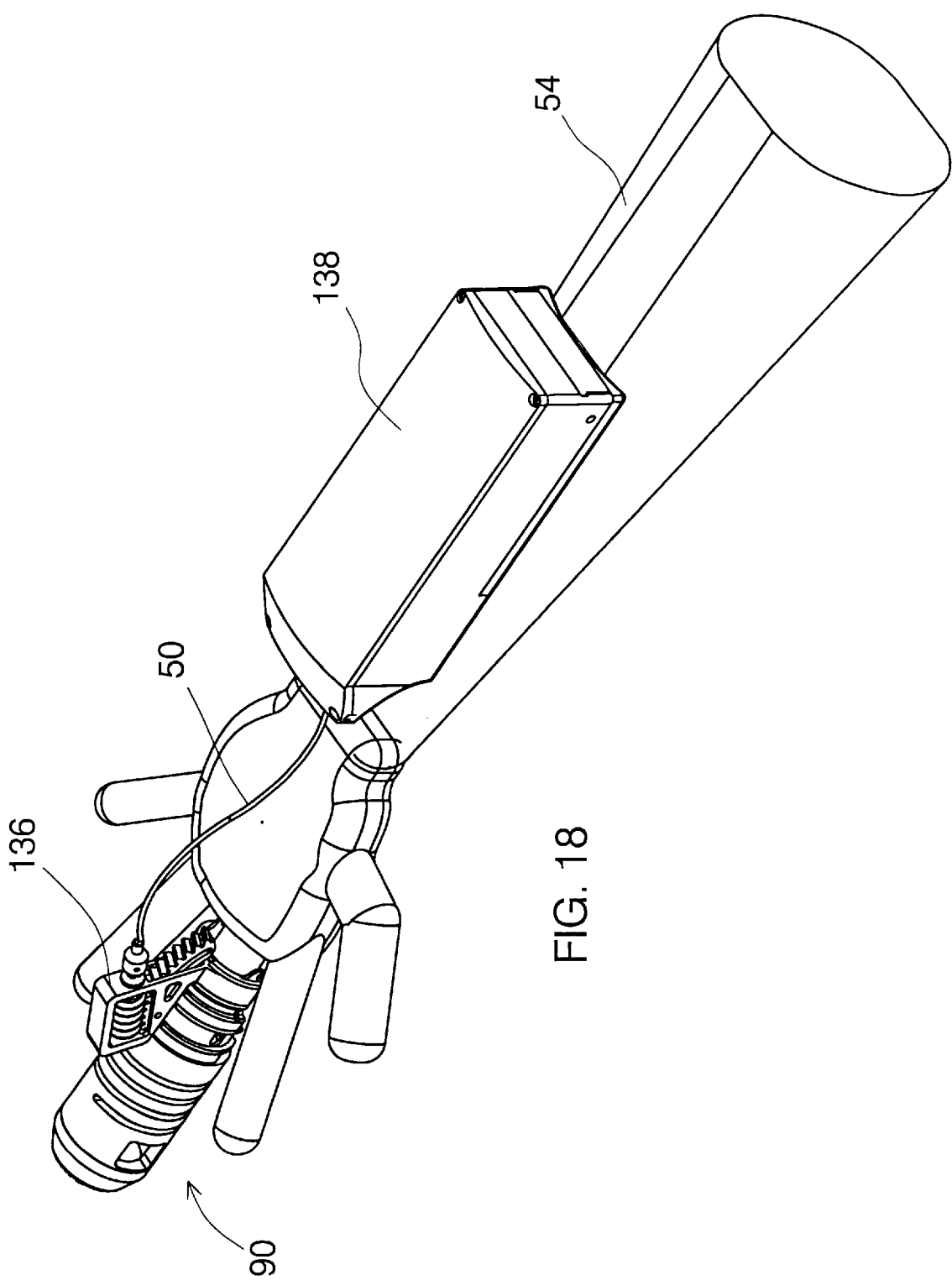
FIG. 18 is a schematic isometric view of the device of FIG. 12 in use.
Figure 19:
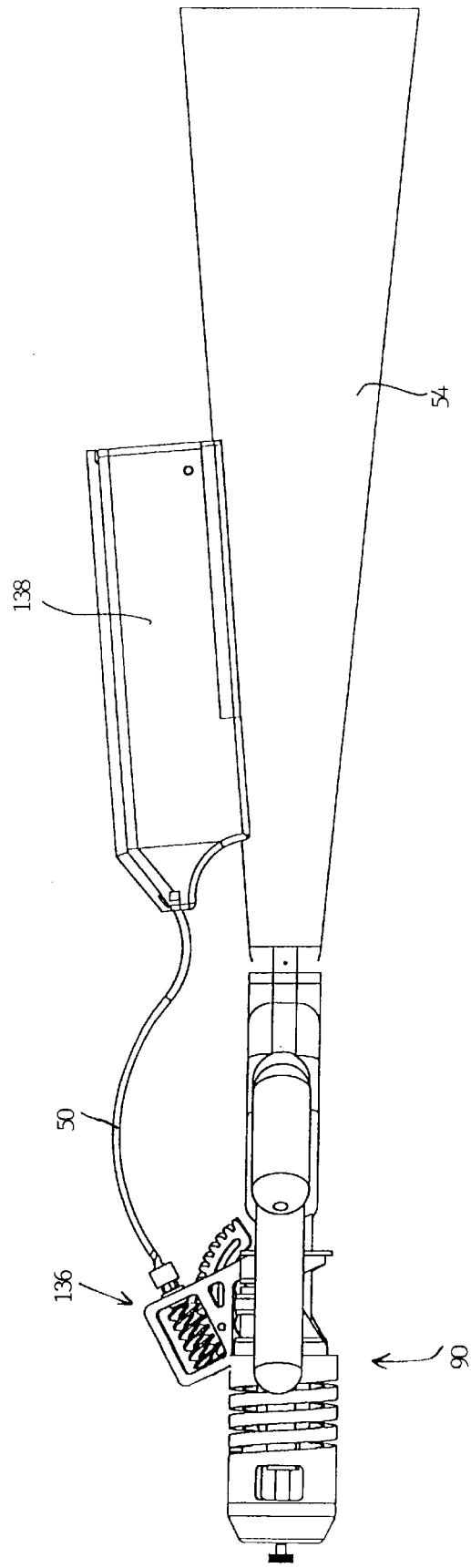
FIG. 19 is a schematic side view of the device of FIG. 12 in use.

Turning now briefly to FIG. 17, this shows a template 140 which is preferably used for precise positioning of the pins 92 and 94. As mentioned earlier, the elasticity of the devices of the present invention makes the positioning of the pins much less critical than in the prior art devices. However, particularly in the case of an injured finger where the entire region surrounding the injury is typically sensitive, it is important to position the pins centrally so that the device does not touch the skin near the injured joint. For this purpose, template 140 is produced with alignment bores 142 and 144 spaced on either side of a hinge 146 to correspond to the desired initial spacing of pins 92 and 94. Alignment bores 142 and 144 serve as drill guides for proper insertion of the pins.

Figure 20:
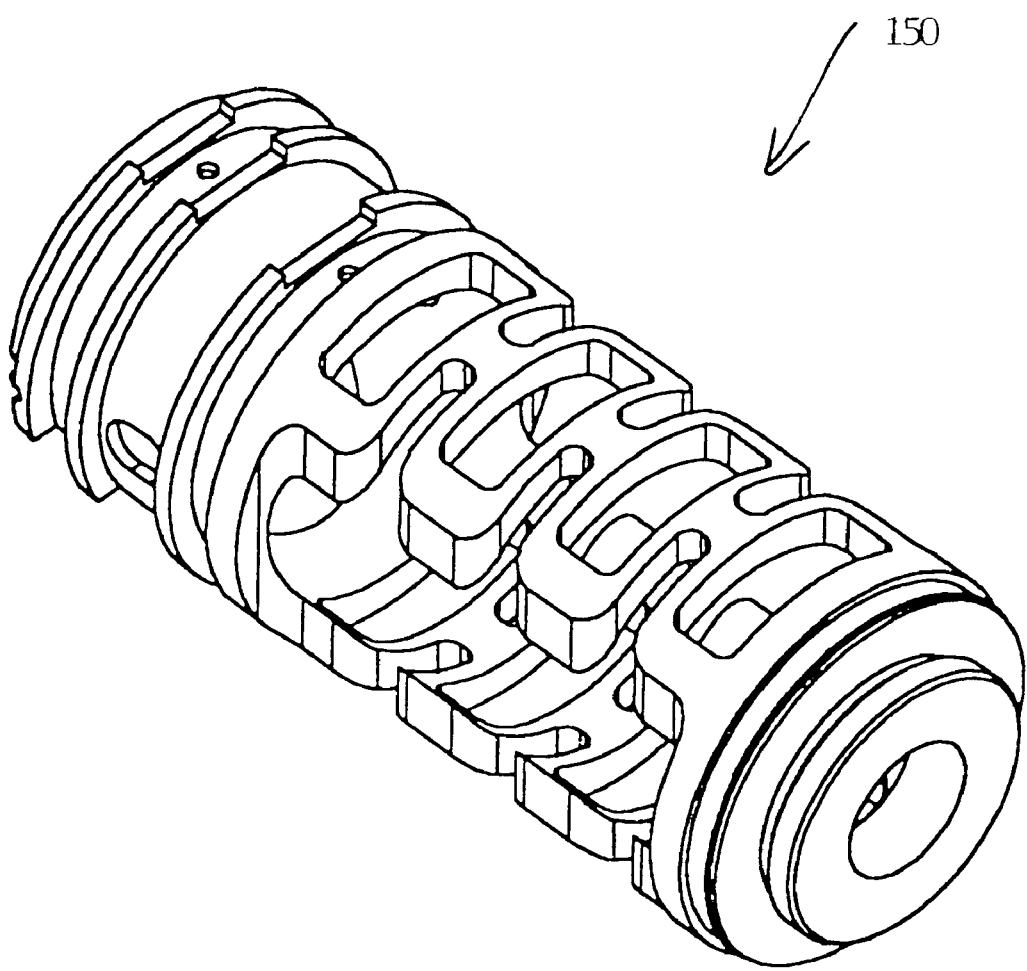
FIG. 20 is an isometric view of an alternative spring element for use in the device of FIG. 12.

Finally, with reference to FIG. 20, it should be appreciated that the spring structure of distal section 106 need not be helical and may take any of a wide range of forms. By way of example, FIG. 20 shows an alternative spring structure 150 for use as part of distal section 106. The open sides of this structure minimize the bulk of device 90 between the injured finger and adjacent fingers, making the device more comfortable for the patient.

It will be appreciated that the above descriptions are intended only to serve as examples, and that many other embodiments are possible within the spirit and the scope of the present invention.

What is claimed is:

1. A device for generating passive motion of a joint while applying traction, the joint having been prepared by insertion of pins into a proximal and a distal bone adjacent to the joint, the device comprising:

(a) a proximal bracket for engaging the pin of the proximal bone;

(b) a distal bracket for engaging the pin of the distal bone; and (c) a tension-hinge mechanism connecting between said proximal bracket and said distal bracket, said tension-hinge mechanism including:

(i) a hinge for permitting rotational movement of said distal bracket relative to said proximal bracket, and (ii) an adjustment mechanism for allowing substantially continuous adjustment of the distance between said hinge and at least one of said proximal bracket and said distal bracket so as to apply tension across the joint, said adjustment mechanism including an elastic element deployed so as to allow elastic variation of the distance between said proximal bracket and said distal bracket.

2. The device of claim 1, wherein said adjustment mechanism includes a counter-threaded bolt, said counter-threaded bolt serving as a central pin for said hinge.

3. The device of claim 2, wherein said counter-threaded bolt forms part of a scissors mechanism.

4. The device of claim 1, further comprising an actuator mechanism deployed between said proximal bracket and said distal bracket for generating relative rotation between said proximal bracket and said distal bracket about said hinge.

5. The device of claim 4, wherein said actuator mechanism includes a gear member attached to one of said proximal bracket and said distal bracket and a worm gear mounted with an axis of rotation fixed relative to the other of said proximal bracket and said distal bracket, said worm gear being engaged with said gear member.

6. The device of claim 1, wherein said adjustment mechanism includes a gauge for indicating a state of adjustment of said adjustment mechanism.

7. The device of claim 1, wherein the joint is a wrist joint, wherein said proximal bracket includes upper and lower abutment surfaces for abutting upper and lower surfaces of a forearm of a patient and said distal bracket includes upper and lower abutment surfaces for abutting upper and lower surfaces of a hand of the patient.

* * * * *